United States Patent [19]

Stumm

[11] 4,447,778
[45] May 8, 1984

[54] APPARATUS FOR SECURING STORAGE TAPE ON A TEST PIECE DURING MAGNETOGRAHIC TESTING

[75] Inventor: Wolfgang Stumm, Reutlingen, Fed. Rep. of Germany

[73] Assignee: Institut Dr. Friedrich Förster Prüfgerätebau, Reutlingen, Fed. Rep. of Germany

[21] Appl. No.: 275,318

[22] Filed: Jun. 19, 1981

[30] Foreign Application Priority Data

Jul. 12, 1980 [DE] Fed. Rep. of Germany ....... 3026540

[51] Int. Cl.³ .................. G01N 27/85; G01R 33/10
[52] U.S. Cl. ................................ 324/213; 324/226; 324/262
[58] Field of Search ................... 324/213–216, 324/229–231, 261, 262, 226

[56] References Cited

U.S. PATENT DOCUMENTS

| 2,665,333 | 1/1954 | Dunipace et al. | 324/231 |
| 2,764,733 | 9/1956 | Forest | 324/213 |
| 3,430,133 | 2/1969 | Greiner et al. | 324/213 |
| 3,513,555 | 5/1970 | Vachon | 324/231 X |
| 3,528,002 | 9/1970 | Dunleavy | 324/231 |
| 4,063,157 | 12/1977 | Lorenzi et al. | 324/213 |

FOREIGN PATENT DOCUMENTS

| 2352511 | 4/1975 | Fed. Rep. of Germany | 324/213 |
| 1237864 | 6/1971 | United Kingdom | 324/213 |

Primary Examiner—Gerard R. Strecker
Attorney, Agent, or Firm—George J. Netter

[57] ABSTRACT

Method and apparatus for magnetographic testing of magnetizable test pieces including pressing a magnetic storage tape upon the test piece, magnetizing the test piece thereof while the tape is being pressed against the test piece surface, removing the tape and scanning the tape by means of a probe which responds to magnetic forces to detect any stored defect stray fluxes.

4 Claims, 4 Drawing Figures

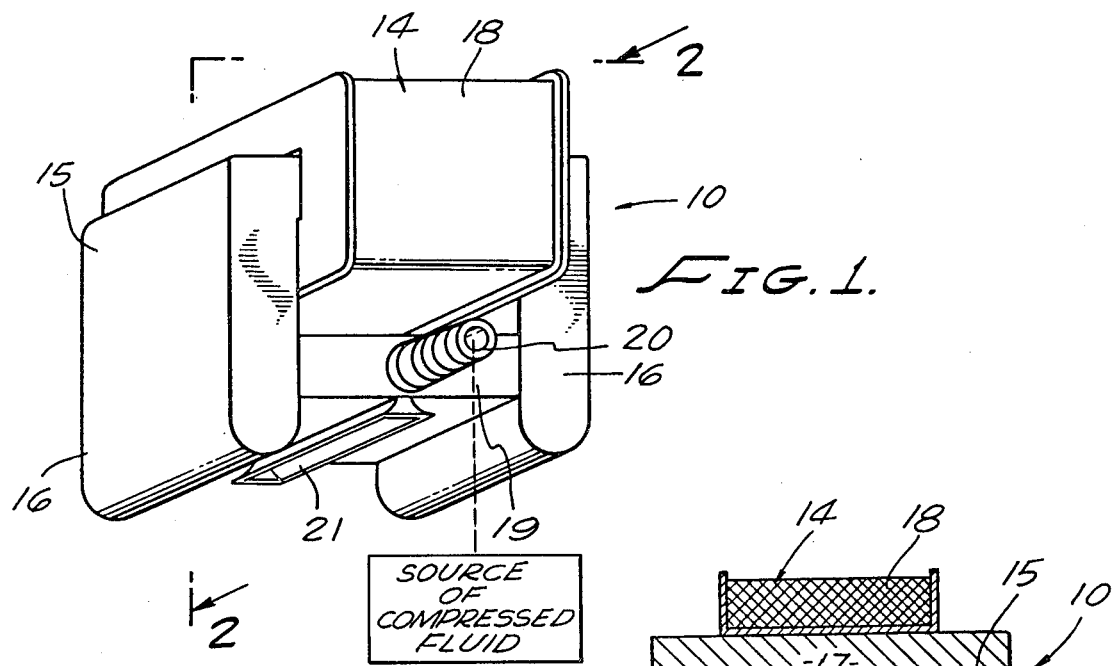
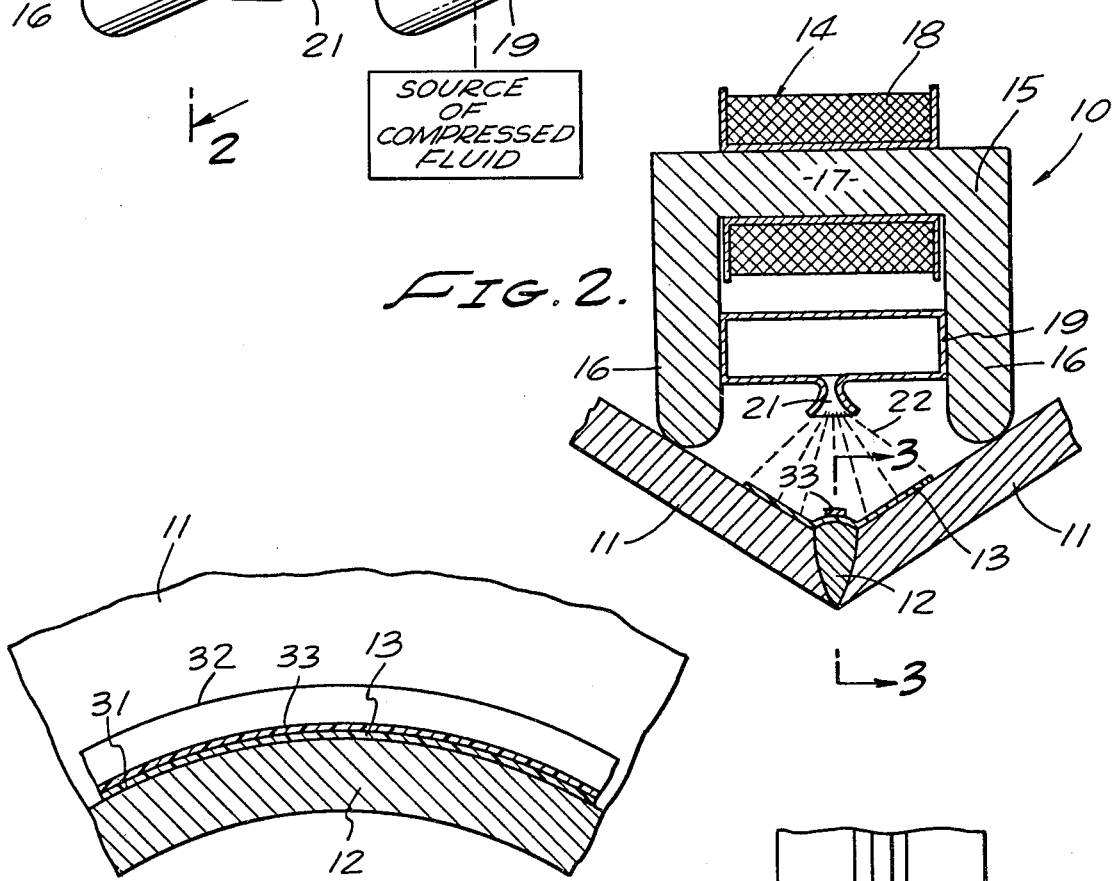
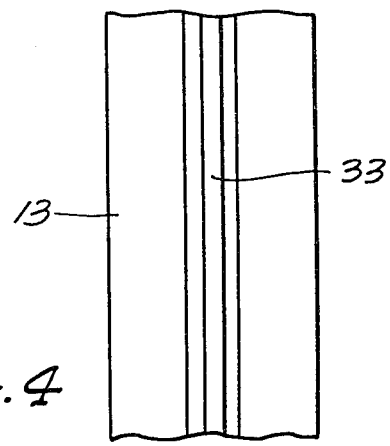

APPARATUS FOR SECURING STORAGE TAPE ON A TEST PIECE DURING MAGNETOGRAHIC TESTING

The present invention relates generally to a method and apparatus for magnetographic testing of magnetizable test pieces including pressing a magnetic storage tape upon the test piece, magnetizing the test piece thereof while the tape is being pressed against the test piece surface, removing the tape and scanning it by means of a probe which responds to magnetic forces to detect any stored defect stray fluxes.

BACKGROUND

For a number of years magnetography has been used with increasing frequency and satisfactory success in non-destructive material testing. Recently, it has also been used for detecting defects in welding seams of complex shapes on pipe constructions on underwater drilling platforms. In this case, tests to be carried out below sea level are made by divers.

Among other advantages offered by the magnetography, its increasing popularity is due primarily to the high sensitivity achieved by its use, which sensitivity results from the fact that the magnetography offers far better possibilities than all the other scanning magnetic stray flux testing methods to scan the stray flux in the immediate neighborhood of the test piece surface.

As compared to the well-known magnetic-powder testing method, which likewise offers high sensitivity, magnetography has the advantage that indications as to the depth of the defect can be derived from the defect signal amplitude. However, both the sensitivity and the correlation between defect signal amplitude and defect depth are confined to certain limits. While in the case of level or uniformly curved surfaces, the flexible storage tape adapts itself ideally to the shape of the surface, this is not possible to the same degree in the case of nonuniformly curved or irregular surfaces. Here, the testing quality depends on whether or not and to what degree the storage tape can be pressed into the irregularities of the surface during the magnetization process. According to one known technique, this can be done by means of contact rollers which may be provided with a specific surface profile. Apart from the fact that frequently the use of such contact rollers is impossible, for instance in cases where magnetic pulses are used for the magnetizing process, they also often fail to achieve a sufficiently intimate contact between the storage tape and the test piece surface, in particular when irregularities with small radii of curvature are encountered on the surface. In addition, handling of the contact rollers is complicated, which makes them often undesirable. The same applies also to the use of brushes as a contact medium.

In accordance with another known process, the strip-shaped conductor used for magnetizing the test piece includes an expanded rubber lining serving to press the flexible storage tape against the test piece surface when the conductor is applied to the latter to effect the magnetization. But, of course, this method also does not enable the storage tape to be pressed into sharp-edged irregularities in the surface.

OBJECT AND SUMMARY

It is a primary object of the present invention to provide a method and apparatus for carrying out this method, that give better results than the methods known heretofore in establishing excellent contact between the flexible magnetic storage tape and the surface of the test piece, even at critical points.

While the means, for instance an expanded rubber item used heretofore for pressing the storage tape against the test piece surface, permitted only limited deformation of its contact surface, a jet of liquid or gas used for this purpose in the present invention which is not subjected to any such limitation. The dynamic pressure generated when the jet hits the storage tape causes high forces to act on any point of the storage tape so that the latter adapts itself almost ideally to the test piece surface. Best results are achieved when the magnetic storage tape exhibits minimum thickness and maximum elasticity or flexibility.

In one advantageous embodiment of the invention, which is of particular interest for underwater applications, the liquid or gas jet is switched on shortly before and switched off shortly after the magnetizing pulse. This limits the energy requirements to a minimum. The apparatus for carrying out the invention offers the particular advantage that the means for pressing the storage tape against the test piece surface are integrated into the magnetizing yoke so that the need to manipulate additional contact pressure means is eliminated. This is of great importance especially in underwater applications.

According to a further embodiment of the invention, only one triggering action is required for the two operations of pressing the storage tape against the test piece surface and magnetizing the test piece. Another version insures excellent correlation between the storage location of the defect signal in the storage tape and the location of the defect in the test piece, even in the case of very irregularly curved test piece areas.

In underwater applications, the water jet used for pressing the storage tape against the test piece surface can be advantageously produced either by the use of a simple pump, or with particular advantage by the use of compressed air. In this latter case, a flooding vessel provided with flooding valves which permit quick venting of the vessel is arranged between the nozzle arrangement and the compressed-gas source. The compressed-gas source consists in this case preferably of a separate small compressed-air cylinder. The water quantity contained in the flooding vessel, or better part thereof, produces an intimate contact between the storage tape and the test piece surface during the magnetizing period. The contact is achieved by causing a predetermined quantity of compressed air to flow through an inlet valve into the flooding vessel, with the flooding valves closed. This compressed air presses a corresponding quantity of water through the nozzle arrangement and out of the flooding vessel, thus producing the water jet required for pressing the storage tape against the test piece surface. At the end of the magnetizing period, the flooding vessel is vented. To this end, the flooding valves of the flooding vessel are opened for a short period of time to enable the vessel to be filled with the water necessary for producing the next water jet. By correctly dosing the compressed-air pulse, any penetration of the compressed air into the nozzle arrangement and, thus, the formation of air bubbles in the nozzle area are prevented.

The repulsion momentum produced by the water jet can be eliminated by at least one additional water jet directed in the opposite direction. This may be achieved by one or more additional nozzles which are also connected to the nozzle arrangement and the resulting counter-momentum of which is equal to the repulsion momentum but acts in the direction opposite the direction in which the tape is being pressed. If the counter-momentum is produced by a plurality of nozzles, the arrangement of the latter may be selected so as to prevent any incommodation of the diver operating the apparatus by the water jets produced by them.

DESCRIPTION OF THE DRAWING

FIG. 1 is a perspective view of one embodiment of the apparatus for practicing the method of the invention.

FIG. 2 shows a sectional, elevational view of the apparatus taken along line 2—2 of FIG. 1.

FIG. 3 shows a sectional view taken along the line 3—3 of FIG. 2.

FIG. 4 shows a magnetic storage tape.

DESCRIPTION OF PREFERRED EMBODIMENTS

FIGS. 1 and 2 show by way of example an apparatus 10 in accordance with the invention which may be used for testing submerged welding seams of the pipe construction of an underwater mineral drilling platform and which uses the surrounding sea water as a medium for pressing the magnetic storage tape against the test piece surface. This apparatus may be similarly employed, also, for carrying out magnetographic tests in other fields, and other media, such as compressed air, may be used in those cases as the pressure exerting means. The apparatus 10 serves, on the one hand, for magnetizing steel sheets 11 and a welding seam 12, and, on the other hand, for pressing an elastic, flexible magnetic storage tape 13 against the areas of the test piece 11 to be tested, and all without any physical contact between the apparatus 10 and the storage tape 13. The magnetizing means 14 of the apparatus 10 includes essentially a magnet yoke 15 having pole shoes 16 and a yoke coil 18 inductively wound around the yoke core 17, the yoke coil 18 being fully insulated for this particular application.

For ease of description here, a handle serving to manipulate the apparatus 10 is not shown in the drawing. Likewise, not shown in the drawing is the conventional power pack supplying the necessary magnetizing current and control means for the pulsing operation, the connection cable for connecting the power pack to the apparatus 10 and a triggering lever near the handle which will be discussed in greater detail below. The pole shoes 16 enclose between them a pressure vessel 19 provided at its front with a hose bit or fitting 20 for connection with a pressure hose through which pressurized water is supplied to the unit. The bottom face of the pressure vessel 19 is equipped with an elongated nozzle 21 having a length approximately equal to the length of the pole shoes 16. This nozzle 21 serves to produce a water jet 22 to press the storage tape 13 into all irregularities of the surface of the test piece 11.

The pressurized water source consists of a small pump which may be located near the magnetizing power pack and which is connected to the pressure vessel 19 via the hose nipple 20 and a pressure hose. In most applications, a pump with a connected load in the range of several hundred watts should be sufficient. This pump need not operate continuously, but may rather be switched on shortly before each magnetizing pulse. This is achieved by actuating the triggering lever which is arranged near the manipulating handle for the apparatus 10 and which serves simultaneously to switch on the pump and—with a specified delay—to produce a magnetic pulse from the magnetizing power pack.

If the area to be tested is of a certain length, one first attaches the ends of the storage tape 13 to the test piece 11 so that the area to be tested is covered by the tape. When, the apparatus 10 is placed upon the test piece surface, proceeding in overlapping steps, which may conveniently be marked on the storage tape 13, and actuating the triggering lever one each time the apparatus is brought into contact with the test piece surface. Finally, the storage tape 13 is removed for being scanned outside the water by means of a magnetic sensor provided for this purpose. If the beginning and the end of the storage tape 13 have been previously marked on the test piece surface, detect signals recorded in the storage tape can be correlated without any difficulty to the location of the defects in the test piece surface.

In cases where the test piece surface exhibits curvatures or bends which extend in more than one axial direction, the flexibility and elasticity of the storage tape 13 and the water jet 22 used as pressure agent still insure an intimate contact between the storage tape 13 and the test piece surface, but because of the elasticity of the storage tape and correlation between the location of the defect and the storage location of the associated defect signal may no longer be insured. To eliminate this disadvantage, it has been assumed that in all imaginable applications there always exists one line along which the storage tape need not be extensible. FIG. 3 shows a symmetrical section through the welding seam 12 of the test piece 11. It appears that the storage tape 13 need not be extended along the sectional line 31 which follows the uppermost point of the welding seam 12, while the marginal lines 32 of the storage tape 13 are subjected to a considerable degree of extension. In the present case, the storage tape 13 is provided on its upper face opposite the line 31 with a small inelastic strip 33 which does not distort and which insures that the correlation between the location of the defect and the storage location is fully retained at least in the central area of the storage tape 13. Generally, the inelastic strip 13 will always be arranged along the line of minimum length of the test piece surface, measured in the direction of the longitudinal extension of the storage tape.

FIG. 4 shows once more the storage tape 13 equipped with the inelastic central strip 33. The strip 33 may be fixed to the storage tape 13 by vulcanizing, but the use of an elastic bonding agent or in any other convenient manner. Also, the completely inelastic strip 33 may be replaced by a strip of an elasticity considerably lower than that of the storage tape.

What I claim is:

1. Apparatus for magnetographic testing areas of a magnetizable test piece including an elongated flexible elastic magnetic storage tape overlying the magnetizable test piece, magnetizing means with a yoke and two pole shoes for introducing magnetic flux into the test piece, an energizing coil encircling the yoke, a source of electric current, and means for connecting the yoke coil to the electric current source, comprising:

means carried by and located between the pole shoes, said means being made of a stable shape material to encircle a certain volume of fluid, and having a nozzle facing toward the storage tape overlying the test piece;

a source of compressed fluid; and means interconnecting the source of compressed fluid to the means carried by and located between the pole shoes for directing the compressed fluid onto the storage tape and forcing said tape into continuous intimate contact with the test piece.

2. Apparatus as in claim 1, in which the means carried by the pole shoes include a pressure vessel equipped with a hose nipple as inlet and an oblong nozzle-type orifice as outlet forming said nozzle, said oblong nozzle-type orifice being oriented along the said elongated storage tape.

3. Apparatus as in claim 1, in which the flexible elastic magnetic storage tape includes at least one substantially inelastic strip.

4. Apparatus as in claim 1, in which the pole shoes are arranged such that the magnetic flux is oriented perpendicular to the elongated tape.

* * * * *